United States Patent [19]
Kirk et al.

[11] Patent Number: 4,892,889
[45] Date of Patent: Jan. 9, 1990

[54] PROCESS FOR MAKING A SPRAY-DRIED, DIRECTLY-COMPRESSIBLE VITAMIN POWDER COMPRISING UNHYDROLYZED GELATIN

[75] Inventors: Paula S. Kirk, Dearborn Heights; Dale R. Olson, Riverview, both of Mich.

[73] Assignee: BASF Corporation, Parsippany, N.J.

[21] Appl. No.: 104,446

[22] Filed: Oct. 2, 1987

Related U.S. Application Data

[63] Continuation-in-part of Ser. No. 932,164, Nov. 18, 1986, abandoned.

[51] Int. Cl.$^4$ .................... A61K 47/00; A61K 31/07; A61K 31/355; A61K 31/59; A61K 31/015
[52] U.S. Cl. .................... 514/774; 514/775; 514/777; 514/778; 514/786; 514/725; 514/167; 514/458; 514/765
[58] Field of Search ............... 424/499, 500; 514/458, 514/944, 774, 775, 777, 778, 786, 725, 167, 765

[56] References Cited

U.S. PATENT DOCUMENTS

| | | | |
|---|---|---|---|
| 2,824,807 | 2/1958 | Laster et al. | 424/499 |
| 3,869,539 | 3/1975 | Kring et al. | 514/458 |
| 4,254,100 | 3/1981 | Keller et al. | 424/500 |
| 4,395,422 | 7/1983 | Schmidt | 424/284 |
| 4,519,961 | 5/1985 | Schumacher et la. | 424/499 |

OTHER PUBLICATIONS

Chem. Abst. 85:166566(u) (1976)–Georgakopoulos et al.
Chem. Abst. 91:162,992(f) (1979)–Georgakopoulos et al.

Primary Examiner—Douglas W. Robinson
Assistant Examiner—Raymond J. Henley, III
Attorney, Agent, or Firm—Rupert B. Hurley, Jr.

[57] ABSTRACT

A process for making a directly-compressible vitamin powder utilizes a conventional spray-dryer. The resulting powder is comprised of a fat-soluble vitamin, a water-soluble carbohydrate, and a gelatin having a bloom number between 30 and 300.

11 Claims, No Drawings

PROCESS FOR MAKING A SPRAY-DRIED, DIRECTLY-COMPRESSIBLE VITAMIN POWDER COMPRISING UNHYDROLYZED GELATIN

This application is a continuation-in-part of Ser. No. 06/932,164 filed Nov. 18, 1986 now abandoned.

BACKGROUND OF THE INVENTION

1. Field of the Invention

The present invention pertains to processes for making formulations useful for direct-compression powders. These powders are used in the manufacture of pharmaceutical tablets. More specifically, the present invention is concerned with processes for making directly-compressible formulations which also contain a fat-soluble vitamin. It has been found that the use of a unhydrolyzed gelatin (i.e. a gelatin having a bloom number between 30 and 300) in these tabletting formulations imparts satisfactory hardness to tablets made therefrom, and that emulsions made with unhydrolyzed gelatin do not exhibit off-odor problems. Moreover, it has unexpectedly been found that a mixture comprising an unhydrolyzed gelatin can be spray-dryed by conventional means.

DESCRIPTION OF THE PRIOR ART

The closest art known to Applicants is: U.S. Pat. Nos. 4,395,422; 2,824,807; 4,254,100; 4,519,961; 3,914,430; 3,608,083, and an article entitled 'The Effects of Using Different Grades PVP and Gelatin as Binders in the Fluidized Bed Granulation of Tabletting of Lactose'. *Pharmazie*, 38 (4), 240–3.

The process described in the '422 patent produces a product comprising Vitamin E and a hydrolyzed (i.e. zero bloom) gelatin. The '430 and '083 patents describe similar processes (i.e. both of these patents utilize only zero bloom gelatin in their processes).

The '807 patent teaches a process for spray-drying a solution of an unhydrolyzed gelatin by "atomizing the solution into a cool air zone prior to introduction of the atomized solution into a drying zone". (U.S. Pat. No. 2,824,807, claim 1). The '807 patent refers to problems encountered in spray-drying solutions of high bloom gelatins (Column 1, 1. 36—column 2, 1. 20). As a result of these problems, the '807 patent states that if the high bloom gelatin concentration is greater than 1 percent, satisfactory spray-drying cannot be achieved without utilizing the cool air zone modified spray-drying technique disclosed therein.

In contrast, the process of the present invention requires that the spray-drying is carried out in a "conventional" spray-dryer, i.e. without any means to overcome the problems described in the '807 patent. Applicants have unexpectedly found that when utilizing the mixture described below, no droplet formation problems were encountered during spray-drying, even though the mixture comprised significantly more than 1 percent of a high bloom gelatin.

The article cited above, authorized by Georgakopoulos et al, teaches a fluid-bed granulation process for making a tabletting composition comprising a high bloom gelatin, lactose, and a fat soluble vitamin. In contrast, the process of the present invention pertains to spray-drying, not fluid-bed granualtion.

The '100 patent, to Keller, teaches processes for making tabletting compositions which comprise fat-soluble vitamins and high bloom gelatins. The '100 patent nowhere refers to spray drying, but rather teaches emulsification followed by filtration and either fluid-bed drying or vacuum drying.

The '961 patent, to Schumacher, teaches processes for making powders which comprise a fat-soluble vitamin and a high bloom gelatin. The processes referred to in the '961 patent utilize "spray formulation" followed by fluid bed drying. During spray formulation the temperature of the gas flowing through the spraying chamber is at, or near, room temperature. In the '961 patent, the "drying" of the powder is carried out by heating the powder in a fluid bed for relatively long periods of time. In contrast, conventional spray drying utilizes a comparatively high temperature gas in the spray chamber, and the desired amount of drying is completed quickly, i.e. in less than 10 seconds.

BRIEF SUMMARY OF THE INVENTION

The present invention pertains to a process for making a spray-dried vitamin powder. The spray-dried vitamin powder is a component which can be used in a formulation suitable for direct-compression into tablets. The process of the present invention is carried out by combining a fat-soluble vitamin, a gelatin having a bloom number between 30 and 300, a water-soluble carbohydrate, and an effective amount of water to permit spray-drying. Once combined, the vitamin, gelatin, carbohydrate, and water together form a mixture. The relative amounts of vitamin, gelatin, and carbohydrate in the mixture are selected so that the resulting spray-dried powder comprises:

(1) 20 to 60 percent by weight of the fat-soluble vitamins;

(2) 6 to 46 percent by weight of the gelatin; and (3) an effective amount of the carbohydrate to prevent extrusion.

The mixture is spray-dried in a conventional spray dryer.

It is an object of the present invention to provide a process for producing a spray-dried directly-compressible, fat-soluble vitamin powder which comprises an unhydrolyzed gelatin, while using a conventional spray-dryer.

It is a further object of the present invention to provide a process for producing a spray-dried, directly-compressible powder comprising vitamin E and unhydrolyzed gelatin, the powder being suitable as a component in a formulation which can be directly compressed into a tablet, the process using a conventional spray dryer.

It is an object of the present invention to enable one to carry out the conventional spray-drying of a solution comprising substantially more than one percent by weight of an unhydrolyzed gelatin, without encountering problems with droplet formation as described by Laster in U.S. Pat. No. 2,824,807.

Finally, it is an object of the present invention to enable the spray-drying of a solution comprising a substantial amount of a high bloom gelatin using only conventional spray-drying means.

DETAILED DESCRIPTION OF THE PREFERRED EMBODIMENTS

The present invention relates to processes for making spray-dried vitamin powders which comprise a fat-soluble vitamin The four most common fat-soluble vitamins are: vitamin A (retinol), vitamin D (calciferol), vitamin E (tocopherol), and vitamin K (phylloquinone and menaquinone). In the process of the present invention, the vitamin itself, in combination with other ingredients, is spray-dried in a conventional spray dryer. As used herein, the term "conventional spray-dryer" is used with reference to spray-dryers which have no special means for preventing the formation of the "fluffy web-like mass of gelatin", and the gelatin "filaments", referred to in the Laster patent (U.S. Pat. No. 2,824,207). The conventional spray-dryer used in the process of the present invention has no means for preventing the problems referred to in the Laster patent. It has been surprisingly found that no such means is required in the process of the present invention.

Preferably, vitamin E is the vitamin used in the powder of the present invention. Most preferably, the vitamin E is a tocopherol or an ester thereof. Alpha-tocopherol has the greatest biological activity while the isomers beta-, gamma-, and delta-tocopherol have a lesser activity. The tocopherols and their esters such as water tocopherol acetate and tocopherol succinate are normally water insoluble and either oily, waxy, or have a low melting point. Therefore, in making water-dispersible powders, an emulsion is normally prepared and then spray dried. D-alpha-tocopherol and d-alpha-tocopherol acetate are of use in the invention. Preferably used is vitamin E acetate. Most preferably the powder comprises between 50 and 54 percent (by weight) of dl-alpha-tocopherol acetate.

The resulting spray-dried powder of the present invention comprises an unhydrolyzed gelatin. The term "unhydrolyzed" is herein defined as a gelatin having a bloom number between 30 and 300. The term "bloom" as used herein and in the appended claims is defined as the weight in grams required to impress a one-half inch diameter plunger 4 mm into a gelatin solution containing 6 percent solids gelled at 10° C. for 17 hours. A suitable test procedure for determining bloom is outlined in *Industrial Engineering Chemistry*, Analytical Edition, vol. II, page 348, and vol. XVII, page 64. The unhydrolyzed gelatin utilized in the process serves as an encapsulator and a binder. Preferably, the bloom count of the gelatin is approximately 80, and preferably, the resulting spray-dried powder comprises between 7.8 and 46 percent, by weight, gelatin. Most preferably, the resulting spray-dried powder comprises approximately 10 percent by weight qelatin having a bloom number of approximately 80.

An additional encapsulator may also be utilized in the present invention. Most preferably, sodium caseinate is utilized as the additional encapsulator. Furthermore, when sodium caseinate is utilized in the process, it preferably comprises between 3 and 20 percent, by weight, of the resulting spray-dried powder, and most preferably comprises approximately 11 percent by weight, of the powder. Preferably, a spray- dried sodium caseinate is utilized in the process. (See U.S. Patent 4,395,422, column 2, lines 16–32).

An effective amount of a water-soluble carbohydrate is necessary in the process of the present invention. The water-soluble carbohydrate can be lactose, maltodextrin, corn syrup, mannitol, sorbitol, a modified food starch, etc. The water-soluble carbohydrate has been found to aid the unhydrolyzed gelatin in creating a stable emulsion, among other desirable effects. The use of the water-soluble carbohydrate creates a powder which is resistant to "extrusion." Extrusion occurs if the oil separates from the powder during compression of the powder into a tablet. Excessive extrusion is highly undesirable because extrusion results in a loss of vitamin potency. The "effective amount" of the water-soluble carbohydrate is an amount which prevents extrusion from occurring. Generally, the water-soluble carbohydrate comprises 5 to 32 percent, by weight, of the resulting spray-dried powder. Most preferably, the water-soluble carbohydrate comprises approximately 9 percent by weight of the resulting spray-dried powder. Furthermore, the water-soluble carbohydrate is most preferably lactose. Occasionally it is desirable to eliminate lactose from the powder. (See Example 3, which utilizes maltodextrin in place of lactose).

The process of the present invention preferably utilizes a secondary emulsifier and surfactant. The secondary emulsifier used is preferably a fatty acid monoglyceride, which is present in an amount between 0.1 and 6 percent by weight of the resulting spray-dried powder. Most preferable is the use of approximately 1.1 percent, by weight of spray-dried product, of a monoglyceride which is a mixture of glycerol monostearate and glycerol derived from hydrogenated tallow or lard and includes about 10 percent by weight diglyceride. (See U.S. Pat. No. 4,395,422, column 2, lines 40–55).

The most preferred spray-drying process for use in the manufacture of the improved powder of the present invention is described in Example 1 below. As stated in Example 1, silicon dioxide was injected into the spray-drying chamber during the spray-drying process. The amount of silicon dioxide utilized should be such that the resulting spray-dried product comprises between 0.1 and 5.6 percent, by weight, silicon dioxide. The preferred amount of silicon dioxide injected during the spray-drying process is approximately 1.1 percent, by weight, of the resulting spray-dried powder. The silicon dioxide improves the flowability of the resulting powder.

EXAMPLE 1

Monoglyceride (0.6 parts]was added to and dissolved within vitamin E oil (28 parts). The vitamin E oil having mono- glyceride dissolved therein was then added to an emulsion feed tank which contained: 8.5 parts lactose, 10.9 parts caseinate, 4.8 parts 80-bloom gelatin, and 47 parts water. All of the ingredients were then homogenized for approximately 30 minutes, or until the emulsion droplet size reached 1 to 2 microns. Generally, the resulting viscosity was between 460 and 660 cps.

The emulsion was then spray-dried. In the spray-drying process, the emulsion was pumped into the spray-drying chamber. The inlet air temperature in the dryer was about 390° F., and the outlet air temperature was approximately 215° F. Approximately 2.0 percent silicon dioxide was also injected into the spray-drying chamber.

The spray dryer utilized a conventional arrangement of components, and had no special means for preventing droplet formation as, for example, are discussed in column 1, line 36 through column 2, line 20 of U.S. Pat. No. 2,824,807, to Laster.

The resulting powder particles were clear beadlets with a bulk density of approximately 50 grams/100 ml. The powder has good flow characteristics. The powder was comprised of the following ingredients, in the following proportions:

|  | % dry ingredients in spray-dried powder |
|---|---|
| (1) Vitamin E | 51.9 |
| (2) Monoglyceride | 1.1 |
| (3) Lactose | 15.8 |
| (4) Sodium caseinate | 20.2 |
| (5) 80-bloom gelatin | 8.9 |
| (6) Silicon dioxide | 1.0 |

This powder was then tabletted as described below.

The powder resulting from the process described above was utilized as a component in chewable tablet formulation. The tablet formulation was compressed into tablets. The formulation consisted of the following ingredients:

|  | grams/tablet |
|---|---|
| (1) Vitamin E powder made via Example I | 0.412 |
| (2) Cab-O-Sil HS-5 TM | 0.035 |
| (3) Syloid 74 TM | 0.015 |
| (4) Tabletting Sugar | 0.295 |
| (5) Flavor | 0.005 |
| (6) Magnesium Stearate N.F. | 0.002 |

The desired tablet weight of approximately 0.76 grams per tablet was achieved. The tablet had a good friability rating (0.1 percent) as well as acceptable tablet hardness (12-18 scu). The friability and hardness tests are described below.

Hardness Test

The tablet was tested for hardness on a Schleuniger-2E hardness tester. A tablet hardness of 7-20 scu (Strong Cobb Units) was considered acceptable.

Friability Test

Tablet friability (percent weight loss of 20 tablets) was determined on a Vanderkamp Friabilitor with a 25 rpm gear driven motor set for five minutes. Hardness and friability data indicate table integrity and resistance to capping and chipping.

EXAMPLE 2

The process described in Example 1 was carried out again, with the ingredients in the following proportions:

|  | Parts |
|---|---|
| (1) Vitamin E | 26.5 |
| (2) 80-bloom gelatin | 17.4 |
| (3) Lactose | 5.6 |
| (4) Water | 51 |
| (5) Silicon dioxide | 1.1 |

This emulsion did not use sodium caseinate as an encapsulating agent. Instead, a greater amount of gelatin was substituted for caseinate and some of the lactose. Furthermore, the emulsion was stable without the use of monoglyceride. In addition, no off-odors were detected after holding the emulsion at 60° C for several hours, even though the emulsion contained a relatively high proportion of unhydrolyzed gelatin. The resulting spray-dried powder was comprised of the following ingredients, in the following proportions:

|  | % dry ingredients in spray-dried powder |
|---|---|
| (1) Vitamin E | 54 |
| (2) 80-bloom gelatin | 35.5 |
| (3) Lactose | 11.4 |
| (4) Silicon dioxide | 1.0 |

The resulting powder had a bulk density of 45 grams/100 ml, the powder also exhibited good flowability. The powder was tabletted as described in Example 1. The tablet had a hardness of 8-12 scu. The friability rating was 0.0 percent.

EXAMPLE 3

The process described in Example 1 was carried out again except that the following ingredients and proportions were utilized.

|  | Parts |
|---|---|
| (1) Vitamin E | 28.8 |
| (2) Maltodextrin (DE* 5-7) | 11.5 |
| (3) Sodium caseinate | 6.8 |
| (4) 80-bloom gelatin | 5.4 |
| (5) Monoglyceride | .58 |
| (6) Silicon dioxide | 1.1 |
| (7) Water | 47 |

*DE is the dextrose equivalent.

This example illustrates a powder which did not contain lactose. In this example, maltodextrin, a polysaccharide, is substituted for lactose. For certain segments of the population, a lactose-free formulation is desirable, as certain segments of the population are deficient in the enzyme lactase which is used to hydrolyze the disaccharide lactose. Lack of ability to hydrolyze lactose can cause gastrointestinal irritation. For individuals with a lactase deficiency, it is desirable to eliminate lactose from the diet. The resulting spray-dried powder was comprised of the following ingredients, in the following proportions:

|  | % dry ingredients in spray-dried powder |
|---|---|
| (1) Vitamin E | 54.3 |
| (2) Maltodextrin (DE 5-7) | 21.7 |
| (3) Sodium caseinate | 12.8 |
| (4) 80-bloom gelatin | 10.2 |
| (5) Monoglyceride | 1.1 |
| (6) Silicon dioxide | 1.0 |

The powder prepared in Example 3 had a density of 42 g/100 ml and exhibited good flowability. The powder was tabletted as described in Example 1. The resulting tablet had a hardness of 5-6 scu. The friability was 0.0 percent.

EXAMPLE 4

A powder was produced by the process described in Example 1, except that the ingredients and proportions utilized were as follows:

|  | Parts |
|---|---|
| (1) Vitamin E | 28.8 |
| (2) Lactose | 10.1 |
| (3) Sodium caseinate | 2.0 |
| (4) 80-bloom gelatin | 12.1 |

|  | Parts |
|---|---|
| (5) Monoglyceride | 0.64 |
| (6) Silicon dioxide | 0.10 |
| (7) Water | 47 |

Example 4 demonstrates that for the most preferred powder, 2 percent caseinate is the lowest proportion of caseinate that can be used to achieve a stable emulsion. At the 2 percent level, it was found that the sodium caseinate adequately encapsulated the vitamin E oil. At still lower caseinate levels, the emulsion was too viscous for spray-drying. Thus, 2 percent is believed to be the minimum level of caseinate for the process of making the most preferred powder. The resulting spray-dried powder was comprised of the following ingredients, in the following proportions:

|  | % dry ingredients in spray-dried powder |
|---|---|
| (1) Vitamin E | 54.3 |
| (2) Lactose | 19.0 |
| (3) Sodium caseinate | 3.77 |
| (4) 80-bloom gelatin | 22.82 |
| (5) Monoglyceride | 1.13 |
| (6) Silicon dioxide | 1.0 |

The powder had a bulk density of 44 g/100 ml and exhibited good flowability. The powder was tabletted utilizing the formulation of Example 1, and the resulting tablet hardness was 7–10 scu. The tablet friability was 0.0 percent.

EXAMPLE 5

The process described in Example 1 was again carried out, except that the ingredients and proportions were as follows:

|  | Parts |
|---|---|
| (1) Vitamin E | 28.2 |
| (2) Lactose | 9.2 |
| (3) Sodium caseinate | 5.0 |
| (4) 80-bloom gelatin | 7.65 |
| (5) Monoglyceride | 3.0 |
| (6) Silicon dioxide | 1.0 |
| (7) Water | 47 |

This example illustrates a powder which utilizes a high proportion of monoglyceride. Monoglyceride acts as a surfactant in the formation of the oil-in-water emulsion. The resulting spray-dried powder was comprised of the following ingredients, in the following proportions:

|  | % dry ingredients in spray-dried powder |
|---|---|
| (1) Vitamin E | 53.21 |
| (2) Lactose | 17.36 |
| (3) Sodium caseinate | 9.43 |
| (4) 80-bloom gelatin | 14.43 |
| (5) Monoglyceride | 5.66 |
| (6) Silicon dioxide | 1.0 |

The powder had a tapped density of 37 grams/100 milliliters, and exhibited good flowability. Tablet hardness was measured at 7–8 scu, the tablet being made by the formulation utilized in Example 1. The tablets had a friability of 0.0 percent.

EXAMPLE 6

Another powder was made by the process described in Example 1, except that the following ingredients and proportions were utilized:

|  | Parts |
|---|---|
| (1) Vitamin E | 28.6 |
| (2) Lactose | 16.5 |
| (3) Sodium caseinate | 3.76 |
| (4) 80-bloom gelatin | 3.23 |
| (5) Monoglyceride | 0.58 |
| (6) Silicon dioxide | .53 |
| (7) Water | 47 |

After spray drying, the resulting dry powder had the following proportions of ingredients:

|  | % dry ingredients in spray-dried powder |
|---|---|
| (1) Vitamin E | 54.0 |
| (2) Lactose | 31.1 |
| (3) Sodium caseinate | 7.1 |
| (4) 80-bloom gelatin | 6.7 |
| (5) Monoglyceride | 1.1 |
| (6) Silicon dioxide | 1.0 |

This example illustrates a formulation having a relatively high proportion of lactose. Furthermore, this example illustrates that a relatively low proportion of sodium caseinate and gelatin can be utilized. The powder had a tap density of 48 grams/100 ml, and exhibited good flowability.

The powder was utilized to make a tablet via the formulation given in Example 1. The tablet exhibited a hardness of 6–7 scu. The tablet friability was 0.0 percent.

EXAMPLE 7

Another powder was made by the process of Example 1, except that the following ingredients and proportions were utilized:

|  | Parts |
|---|---|
| (1) Vitamin E | 27.6 |
| (2) 200-bloom gelatin | 7.1 |
| (3) Sodium caseinate | 9.5 |
| (4) Lactose | 7.1 |
| (5) Monoglyceride | .60 |
| (6) Silicon dioxide | 1.1 |
| (7) Water | 48 |

This example illustrates a formulation having a gelatin of higher bloom number than the gelatin utilized in Examples 1–6. The spray-drying process resulted in a formulation having the following proportions:

|  | % dry ingredient in spray dried powder |
|---|---|
| (1) Vitamin E | 27.6 |
| (2) 200-bloom gelatin | 7.1 |
| (3) Sodium caseinate | 9.5 |
| (4) Lactose | 7.1 |
| (5) Monoglyceride | 0.59 |
| (6) Silicon dioxide | 2.1 |
| (7) Water | 48 |

The resulting powder had a tapped density of 48 g/100 ml and exhibited good flowability. When the powder was utilized to make a tablet via the formulation of Example 1, The resulting tablet had a hardness of 9-10 scu. The tablet friability was 0.0 percent.

EXAMPLE 8

Another powder was made by the process of Example 1, except that the following ingredients and proportions were utilized.

|  | Parts (in emulsion) |
|---|---|
| (1) Vitamin E | 28.6 |
| (2) 275 Bloom gelatin | 7.1 |
| (3) Sodium caseinate | 9.5 |
| (4) Lactose | 7.1 |
| (5) Monoglyceride | 0.6 |
| (6) Silicon dioxide | 0.53 |
| (7) Water | 48.0 |

The resulting spray-dried powder was comprised of the following ingredients, in the following proportions:

|  | % dry ingredients in spray-dried powder |
|---|---|
| (1) Vitamin E | 55.0 |
| (2) 275 Bloom gelatin | 13.7 |
| (3) Sodium caseinate | 18.2 |
| (4 Lactose | 13.7 |
| (5) Monoglyceride | 1.15 |
| (6) Silicon dioxide | 1.0 |

The resulting powder had a tapped density of 39 grams/100 ml. The powder exhibited good flow. A tablet was made utilizing this powder in the tablet formulation given in Example 1. The tablet had a hardness of approximately 12 scu as measured by the Hardness Test described above. The table friability was 0.02 percent.

The embodiments of the invention in which an exclusive property or privilege is claimed are defined as follows:

1. A process for making a spray-dried vitamin powder suitable for the preparation of direct-compression vitamin tablets, comprising:
   (A) combining:
      (1) a fat-soluble vitamin; and
      (2) a gelatin having a bloom number between 30 and 300; and
      (3) a water-soluble carbohydrate; and
      (4) an effective amount of water to permit spray-drying; so that a mixture is formed;
   (B) spray-drying the mixture in a conventional spray-dryer whereby a directly-compressible powder is formed, the relative amounts of vitamin, gelatin, and carbohydrate in the mixture being selected so that the resulting spray-dried powder comprises:
      (1) 20 to 60 percent by weight of the fat-soluble vitamin; and
      (2) 6 to 46 percent by weight of the gelatin; and
      (3) an effective amount of the carbohydrate to prevent extrusion.

2. The process as described in claim 1 wherein the relative amounts of vitamin, gelatin, and carbohydrate in the mixture are selected so that the resulting spray-dried powder comprises between 5 and 32 percent, by weight, of the carbohydrate.

3. The process as described in claim 1 wherein sodium caseinate is combined with the vitamin, gelatin, carbohydrate, and water, whereby the mixture comprises the vitamin, the gelatin, the carbohydrate, the water, and the caseinate, the relative amount of caseinate in the mixture being selected so that the resulting spray-dried powder comprises between 3 and 20 percent, by weight, of the caseinate.

4. The process as described in claim 2 wherein the water-soluble carbohydrate is a member selected from the group consisting of lactose, maltodextrin, corn syrup, mannitol, sorbitol, and a modified food starch.

5. The process as described in claim 4 wherein the water-soluble carbohydrate is selected from the group consisting of lactose and maltodextrin.

6. The process as described in claim 4 wherein the resulting spray-dried vitamin powder comprises approximately 11 percent, by weight, sodium caseinate and approximately 9 percent, by weight, lactose.

7. The process as described in claim 4 wherein the process further comprises the step of spraying silicon dioxide into the spray-dryer during the spray-drying of the mixture, the spraying of silicon dioxide being at a rate so that the resulting spray-dried powder comprises between 0.1 to 5.6 percent silicon dioxide.

8. The process as described in claim 4 wherein a fatty acid monoglyceride is combined with the vitamin, gelatin, carbohydrate and water, whereby the mixture comprises the vitamin, the gelatin, the carbohydrate, the water, and the fatty acid monoglyceride, the relative amount of the fatty acid monoglyceride in the mixture being selected so that the resulting spray-dried powder comprises between 0.1 and 6 percent, by weight, of the fatty acid monoglyceride.

9. The process as described in claim 7 wherein a fatty acid monoglyceride is combined with the vitamin, gelatin, carbohydrate and water, whereby the mixture comprises the vitamin, the gelatin, the carbohydrate, the water, and the fatty acid monoglyceride, the relative amount of the fatty acid monoglyceride in the mixture being selected so that the resulting spray-dried powder comprises between 0.1 and 6 percent, by weight, of the fatty acid monoglyceride.

10. The process as described in claim 9 wherein the amount of vitamin in the mixture is selected so that the resulting spray-dried vitamin powder comprises between 50 and 54 percent by weight of vitamin.

11. The process as described in claim 10 wherein the resulting spray-dried vitamin powder comprises 7.8 to 46 percent by weight gelatin having a bloom number of approximately 80, 10 to 15 percent by weight sodium caseinate, 7.8 to 13.9 percent lactose, approximately 0.6 percent by weight fatty acid monoglyceride and approximately one percent by weight silicon dioxide.

* * * * *